United States Patent
Klocke et al.

(10) Patent No.: US 10,098,765 B2
(45) Date of Patent: Oct. 16, 2018

(54) IMPLANT AND METHOD FOR PRODUCING THE SAME

(75) Inventors: Bjoern Klocke, Zurich (CH); Alexander Borck, Aurachtal (DE)

(73) Assignee: BIOTRONIK AG, Buelach (CH)

( * ) Notice: Subject to any disclaimer, the term of this patent is extended or adjusted under 35 U.S.C. 154(b) by 616 days.

(21) Appl. No.: 13/306,412

(22) Filed: Nov. 29, 2011

(65) Prior Publication Data
US 2012/0158126 A1 Jun. 21, 2012

Related U.S. Application Data

(60) Provisional application No. 61/423,123, filed on Dec. 15, 2010.

(51) Int. Cl.
*A61F 2/82* (2013.01)
*A61F 2/91* (2013.01)

(52) U.S. Cl.
CPC ........ *A61F 2/91* (2013.01); *A61F 2210/0076* (2013.01); *A61F 2250/0067* (2013.01)

(58) Field of Classification Search
CPC ....................................... A61F 2/82
USPC ....................................... 623/1.42
See application file for complete search history.

(56) References Cited

U.S. PATENT DOCUMENTS

| | | | | |
|---|---|---|---|---|
| 2003/0083646 | A1* | 5/2003 | Sirhan et al. | 604/891.1 |
| 2006/0136048 | A1* | 6/2006 | Pacetti | A61L 31/10 |
| | | | | 623/1.42 |
| 2008/0215139 | A1* | 9/2008 | McMorrow | A61L 31/10 |
| | | | | 623/1.43 |

FOREIGN PATENT DOCUMENTS

WO 03/037223 A1 8/2003

* cited by examiner

*Primary Examiner* — Matthew Schall
(74) *Attorney, Agent, or Firm* — Wagenknecht IP Law Group PC

(57) ABSTRACT

The present invention relates to an implant (10), and particularly to an intraluminal endoprosthesis, comprising a body and at least one abluminal layer (3) disposed on the body, the abluminal layer preferably containing at least one pharmaceutically active substance. In order to protect the abluminal layer (3) from delamination or shearing, the abluminal layer (3) is additionally fastened to the implant body at least in a transition region (7) by way of at least one anchoring layer (5) disposed on the abluminal layer (3). In addition, methods for producing such an implant are described.

13 Claims, 3 Drawing Sheets

IMPLANT AND METHOD FOR PRODUCING THE SAME

CROSS REFERENCE TO RELATED APPLICATIONS

This invention claims benefit of priority to U.S. patent application Ser. No. 61/423,123, filed Dec. 15, 2010; the contents of which are herein incorporated by reference in their entirety.

TECHNICAL FIELD

The present invention relates to an implant, and particularly to an intraluminal endoprosthesis, comprising a body and at least one abluminal layer disposed on the body, said abluminal layer preferably containing at least one pharmaceutically active substance, and to a method for producing such an implant.

BACKGROUND

Medical endoprosthesis or implants for a wide variety of applications are known from the state of the art in great diversity. Implants as defined by the present invention are notably endovascular prostheses, such as stents.

Stents are used in treatments frequently employed today, in particularly in the case of cardiovascular diseases. The stents are used to keep hollow organs clear. They frequently have a body in the shape of an optionally perforated tubular or hollow-cylindrical mesh structure, which is open at both longitudinal ends. The tubular base mesh of such an endoprosthesis is inserted into the hollow organ requiring treatment and supports the hollow organ treated there. Stents have become established in particular for the treatment of blood vessel diseases. Narrowed areas in blood vessels can be expanded and kept open when using stents, optionally adding a balloon catheter, for example, resulting in increased lumen. For example when treating cancer, stents may also be used to keep narrowed air passages (such as the windpipe), bile ducts or the esophagus, which are caused by malignant tumors, open after dilation.

While through the use of stents or other implants, an optimal cross-section of the hollow organ can be achieved, which is primarily necessary for successful treatment, the lasting presence of such a foreign object triggers a cascade of microbiological processes, which favor the inflammation of the hollow organ to be treated or necrotic changes, for example, and due to the formation of plaque may result in gradual blockage of the stent. In the worst case, this change of the hollow organ may cause an occlusion of the hollow organ.

It is desirable to largely avoid the aforementioned inflammation-favoring effect of implants in the future, because this reduces the effectiveness of the implant and may cause further damage to the treated organism.

So-called drug-eluting stents (DES), which release small quantities of pharmaceutical agents such as sirolimus and paclitaxel, are already being used to inhibit the formation of new cells. Such DES are employed in particular for the treatment of coronary heart disease—notably at an increased risk of restenosis (for example in diabetic patients).

Furthermore, it has been shown that abluminally coated DES are conceptually superior to completely coated DES, because they exhibit improved ingrowth behavior. The abluminal layer contains the pharmaceutically active substance, for example sirolimus and paclitaxel. However, tests of abluminally coated stents showed that the layer adhesion of the abluminal layer is poor and may result in regulatory, production-related and possibly even clinical problems.

In order to improve the adhesion of the layer, so far the material parylene has been tested as an adhesion promoter; in addition, plasma treatment has been tested. These methods, however, did not result in any significant improvement in the adhesion of the abluminal coating.

The document U.S. 2008/0206440 A1 describes a bioabsorbable stent comprising struts, each of which contains, abluminally, a pharmaceutical composition, which is encapsulated by a coating, the matrix of which includes antibodies. The antibodies, or antibody fragments, contained in the antibody coating are used to bind antigens of the hollow organ, which are specific to the treated individual. In this way, the ingrowth behavior of the stent into the respective vascular cells is supported.

Document U.S. 2008/0097575 A1 describes a medical device comprising a coating. The coating is designed so that a luminal surface, or a surface coming in contact with blood, is provided for a stent or a stent graft and that, additionally, an outer surface is implemented, which is adjusted to improve the contact between the adjoining tissue and the stent or stent graft. This design of a stent or stent graft does not contain a solution according to which better adhesion of the abluminal layer can be achieved.

SUMMARY

It is therefore the object of the present invention to prevent an abluminal layer from detaching from the surface of the implant body. A further object is to protect the abluminal layer from delamination and shearing in the simplest possible manner. It is thus an object of the invention to create such an implant and provide a simple method for producing such an implant.

The above object is achieved by the implant having a body and at least one abluminal layer disposed on the body, and for the at least one abluminal layer to be additionally fastened in a transition region to the implant body by way of at least one anchoring layer disposed on the abluminal layer, wherein the anchoring layer covers the abluminal layer partially, more specifically in the transition region.

By using an added anchoring layer, which can preferably be degraded, better adhesion of the abluminal layer in the transition region of the implant body is made possible.

The transition region or transition zone denotes an end region of the abluminal layer, which is disposed the farthest in the luminal direction. By arranging the anchoring layer in the transition region, potential attack points on the abluminal layer for delamination or shearing of the abluminal layer are covered by the anchoring layer and are anchored, so that a detachment of the abluminal layer is prevented right from the start. It is advantageous for the anchoring layer to overlap or cover the abluminal layer only in the transition region, because otherwise the release of a pharmaceutically active substance from the abluminal layer cannot occur immediately after it has been inserted in the treated hollow organ, because the anchoring layer would constitute a barrier.

The surface of the abluminal layer covered by the anchoring layer in the transition region is preferably less than 30% of the total surface of the abluminal layer.

As a degradation layer, the anchoring layer can be designed to be particularly endothelialization-friendly by way of mechanical structuring, admixing or surface modification, so as to promote the healing of the implant in the tissue. In particular, the ingrowth behavior of an implant, notably a stent, can be accelerated by the morphology of the surface thereof. For example, certain periodic structures, such as lines, having periodicity lengths ranging from 0.1 µm to 30 µm (laterally) advantageously support the colonization by endothelial cells. The depth of the structures may range between 200 nm and 5 µm. Re-endothelialization is also positively influenced when antibodies, such as anti-CD34, are immobilized on the surface of the anchoring layer. Likewise, arginine-glycine-aspartic acid (RGD) peptide sequences may be immobilized on the surface of the anchoring layer. These peptide chains bind to integrins. This triggers a signal cascade, which causes the migration and subsequent proliferation of target cells.

The advantage of the solution according to the invention is also that the aforementioned technical, regulatory, and clinical problems are reduced or eliminated. The antiproliferative active agents preferably present in the abluminal layer are only released on the tissue side (abluminally) and thus become effective precisely at the intended site. In addition, by skillfully selecting the composition of the anchoring layer, the luminal side of the implant can be optimally adjusted to the luminal conditions of the hollow organ in which the implant is inserted. In addition, the ingrowth behavior of the implant can thus be improved on the luminal side—as compared to a smooth metal surface. In contrast, on an implant that is entirely covered by a drug coating, the endothelial growth is limited to the luminal side.

Given the accelerated healing of the implant according to the invention in the tissue, and the reduction of ingrowth inhibitors, which is possible due to the endothelialization-friendly anchoring layer, it becomes advantageously possible to shorten the dual antiplatelet therapy.

In the present invention, the body of the implant comprises at least part of the implant, preferably the majority of the implant, which brings about the mechanical integrity of the implant.

As described above, it is advantageous for the at least one anchoring layer to be degradable. The at least one anchoring layer is preferably designed so that it degrades more quickly in vivo than the at least one abluminal layer. After implantation (and optionally after ingrowth) of the implant, the quickly degrading anchoring layer is no longer required in terms of the mechanical holding function. Quick degradation of the anchoring layer is therefore definitely advantageous because foreign objects in an organ should generally be avoided, and the anchoring layer covers the abluminal layer provided with the pharmaceutically active substance in the transition region. In this respect, degradation times typically ranging between one day and 6 months are advantageous.

In a preferred embodiment, the at least one anchoring layer extends into the luminal region of the implant. Luminally, the abluminally provided pharmaceutically active substances are not required, so that they are redundant, or even harmful, in this region. Optionally, other pharmaceutically active substances, which differ from the active agents of the abluminal layer, may be used in the anchoring layer.

In a refinement of the present invention, the at least one abluminal layer is joined to the at least one anchoring layer in the transition region by a bond and/or positive engagement. For example, the abluminal layer is initially partially dissolved in the transition region using a solvent, in which the material of the anchoring layer is dissolved. This is achieved in particular by the anchoring layer overlapping the abluminal layer in the transition region. Optionally, the abluminal layer may also be embedded between a first and a second anchoring layer in such a way that the layers overlap in the transition region. In this arrangement, it is advantageous when n abluminal layers are disposed between two of the n+1 anchoring layers in the transition region, with n>=1 and n being an integer. In this way, the anchoring of the abluminal layer is particularly good. As an alternative, it is also possible to use only n anchoring layers, wherein in this case the first abluminal layer disposed directly on the surface of the body in the transition region is not disposed between two anchoring layers, but is only covered by an anchoring layer in the transition region.

In order to create the degradability of the anchoring layer, preferably polymers, for example short-chained PLGA (polylactide-co-glycolide) or P4HB (poly-4-hydroxybutyrate), are used as materials for the anchoring layer. It may also be advantageous to emboss a pattern forming a surface structure and/or to provide a combination with a chemical endothelium promoter (such as cyclic integrin-binding Arg-Gly-Asp peptides, cRGD). As an alternative, the same polymer matrix may be used for the abluminal layer and anchoring layer, wherein the abluminal layer additionally comprises at least one pharmaceutically active substance.

In order to also achieve improved ingrowth behavior of the implant, a further coating is disposed on at least part of the surface of the outer at least one anchoring layer, said further coating preferably comprising endothelial cell capturing (pro-healing) and/or an endothelialization promoter and/or an endothelialization-promoting surface.

Materials that are suited for the abluminal layer and the anchoring layer may contain polymers and/or metals, for example. The layers can be produced from several of these materials. The common characteristic of these materials is the biodegradability thereof. Examples of suitable polymer compounds include polymers from the group consisting of cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephtalate (PET), polymalonic acid (PML), polyanhydrides, polyphosphazenes, polyamino acids and the copolymers thereof, as well as hyaluronic acid. Depending on the desired properties, the polymers may be present in pure form, in derivatized form, in the form of blends or as copolymers. Metallic biodegradable materials are based primarily on magnesium, manganese, tungsten, and iron alloys.

Biodegradation refers to chemical, notably hydrolytic, enzymatic and other metabolic degradation processes in the living organism, which are caused primarily by the body fluids coming in contact with the biodegradable material of the implant and result in a gradual dissolution of the structures of the implant containing the biodegradable material. This process causes the implant to lose the mechanical integrity thereof at some point. A term that is frequently used synonymously with biodegradation is biocorrosion. The term bioresorption encompasses the subsequent resorption of the degradation products by the living organism.

Advantageously, the abluminal layer(s) and the anchoring layer(s) contain a degradable polymer or are made of such a polymer. It is conceivable for the anchoring layer(s) to degrade (i) more quickly, (ii) more slowly or (iii) at the same rate as the abluminal layer. To this end, the degradation speed is controlled by way of the molar mass and the selection of the polymer, advantageously in the range of 1 week to 6 months. Depending on the indication, it (i) is useful when the abluminal layer still has to be fixed to prevent sliding after implantation. Variant (ii) is advantageous when the healing process or endothelialization is to be forced by quickly exposing the surface of the implant body. Finally, option (iii) includes advantages, for example when the same polymers are to be used as part of a simplified process.

The above object is also achieved by a method comprising the following steps:

a) providing the body of the implant,
b) applying the at least one anchoring layer onto at least one transition region of the abluminal layer.

The anchoring layer is applied such that the anchoring layer covers the abluminal layer partially, more specifically in the transition region. The method according to the invention is particularly simple, cost-effective and protects the abluminal layer from delamination and shearing.

Spraying methods, preferably comprising shading, or pipetting methods have proven to be particularly advantageous and simple methods.

The characteristics of further embodiments of the method according to the invention have already been explained above with respect to the implant according to the invention. The corresponding advantages have also been provided, and apply accordingly to the method according to the invention.

The method according to the invention and the implant according to the invention will be described hereinafter in examples based on figures. All characteristics described and/or illustrated form the subject matter of the invention, regardless of their summarization in the claims or dependent claims.

DETAILED DESCRIPTION

Figure 1:
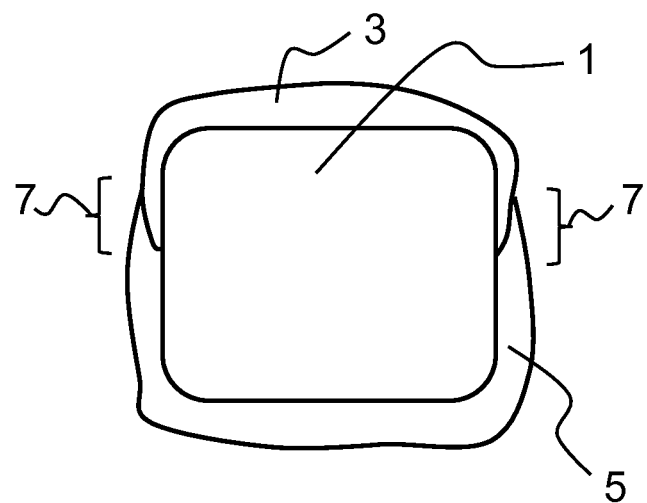
FIGS. 1 to 3 depict embodiments of an implant according to the invention, illustrated based on a cross-section of a stent strut.

FIG. 1 shows the cross-section of a strut 1 of a stent 10. The stent struts can be produced from all commercially available permanent materials, such as CoCr or 316L. In a particular embodiment, the strut may also be made entirely or partially of a biodegradable metal alloy (magnesium, iron, zinc, tungsten, manganese) or a biodegradable polymer. A hollow-cylindrical mesh of struts 1 forms the body of the stent 10. On the surface of the abluminal side of the strut 1, the abluminal layer 3 is disposed, which comprises a PLLA matrix (L210; Boehringer Ingelheim), for example. The matrix contains the pharmaceutically active substance rapamycin in a solids content of 17% to 20% by weight and a surface load of 1.4 µg/mm².

Figure 4:
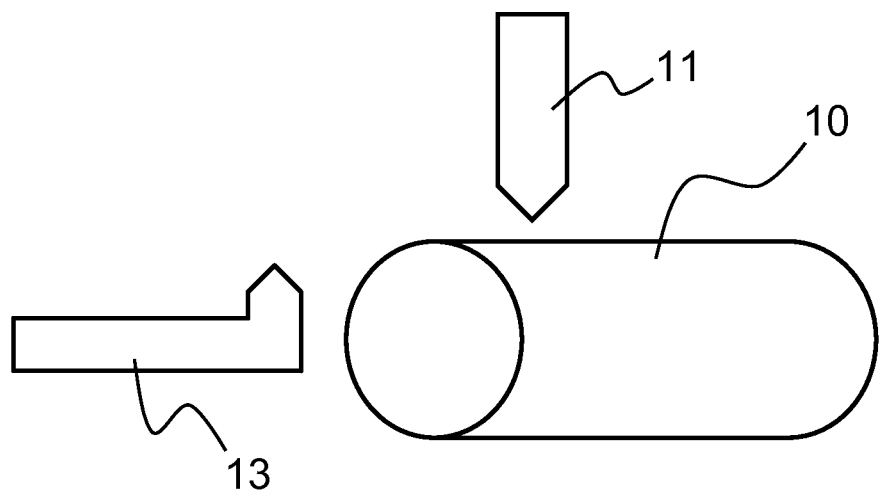
FIGS. 4 to 6 depict three embodiments for applying the anchoring layer as part of the method according to the invention.

The abluminal layer 3 can be produced, for example, using the arrangement shown in FIG. 4.

FIG. 4 shows the outer contour of the stent 10. In order to produce the abluminal layer 3, the hollow-cylindrical mesh of the stent 10 is mounted on a carrier, which is not shown in FIG. 4 and shades the luminal side of the stent 10. On the abluminal side, the polymer provided with the pharmaceutically active substance, (PLGA; LG 858, Boehringer Ingelheim) dissolved in chloroform (concentration 1 g/l), with 17% by weight rapamycin, relative to the solids content, is applied using an abluminally disposed pipetting nozzle 11 directed in the radial direction toward the stent 10. One advantage of this method is that the stent 10 can be coated on all sides.

Prior to pipetting, the stent 10 is measured using a video, after it has been placed onto the cylindrical carrier. Thereafter, a motor-controlled pipetting nozzle 11 is controlled on the basis of the video recording in such a way that the entire outer abluminal surface of the stent 10 is passed over, and the desired mixture made of the pharmaceutically active substance, polymer and solvent, is applied abluminally so as to produce the abluminal layer 3. As an alternative, manual pipetting or turning of the stent body when applying the abluminal layer 3 is also possible.

After the abluminal layer 3 has dried, the luminal coating is produced. For this purpose, a polymer solution comprising PLLA (L210; Boehringer Ingelheim) in chloroform is prepared. The polymer concentration is 1 g/l. Using a further pipetting nozzle 13 directed outwardly in the radial direction, the luminal anchoring layer 5 is applied. To this end, the pipetting nozzle 13 is introduced into the inner hollow space of the hollow-cylindrical mesh of the stent 10.

In the transition region 7, in which the abluminal layer 3 ends in the luminal direction, the abluminal layer 3 is partially dissolved by the solvent of the anchoring layer 5. The material of the anchoring layer 5 is connected at this location to the partially dissolved transition region 7 of the abluminal layer 3. In this way, a particularly firm coupling of the abluminal layer 3 to the anchoring layer 5 is achieved in the transition region 7, so that the abluminal layer 3 is mechanically fastened with particular strength in the transition region 7. In this way, the abluminal layer 3 is better protected against delamination and shearing.

Figure 3:
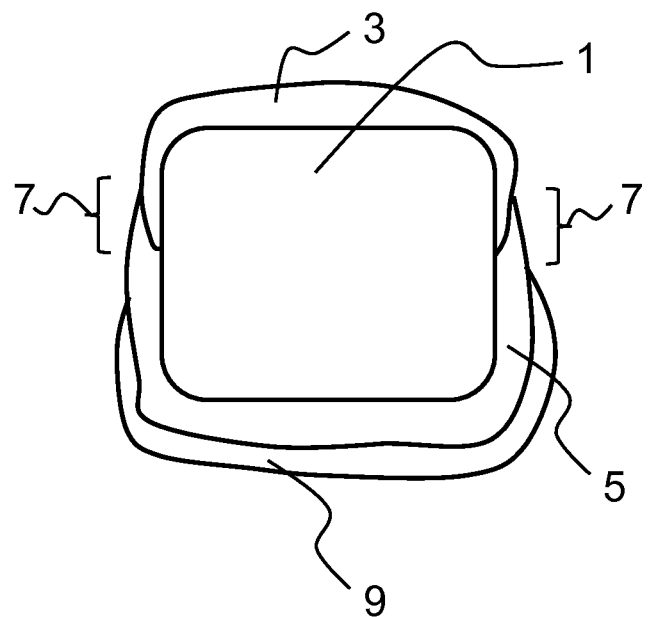

In order to promote the healing of the stent in the tissue, the anchoring layer 5 may be provided with mechanical structures, additives or surface modifications. Such a possibility is shown in FIG. 3. There, the anchoring layer 5 is provided with a further layer 9, which comprises endothelial cell capturing technology. The layer 9 comprises LG 858 or L210 and may be provided with structuring, for example a line structure, preferably by way of an embossing tool. In particular line structures are suited, forming a grid pattern on the surface.

In general, a structure is understood to be a depression in the surface. In the case of a grid structure, depressions are configured in the form of lines, which run in parallel to each other in one direction and form a first family. This first family of periodic depressions is intersected at an angle by other lines, which likewise run in parallel to each other (second family). An angle of intersection of 90° between the first family and second family is preferred.

A person skilled in the art in general knows embossing techniques to produce the structures, notably fine structures. As an alternative, the embossed or unembossed polymer layer 9 may comprise chitosan. The chitosan (KitoZyme, KIOM.CSU) is dissolved in 0.3% acetic acid and sprayed onto the surface. The amine groups of the chitosan allow polymer-analog coupling reactions, notably with isothiocyanate groups. In this way, biomolecules comprising an appropriate anchoring group can be immobilized in an aqueous medium at room temperature.

Figure 2:
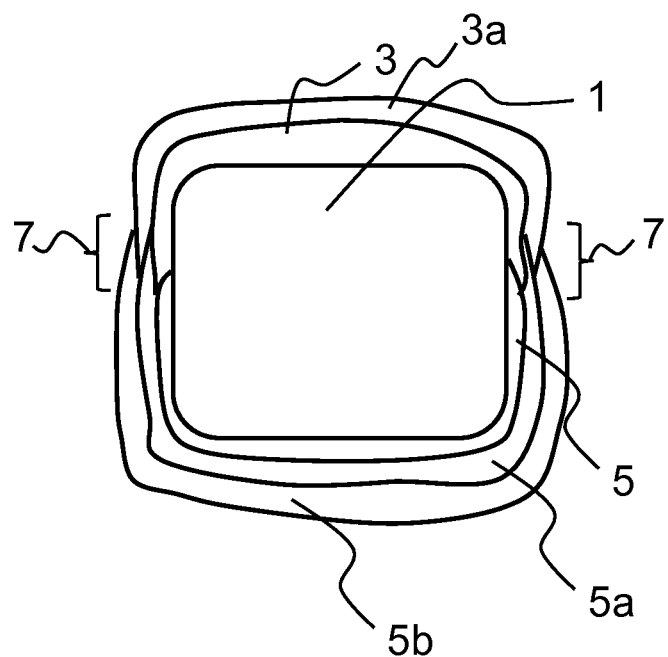

FIG. 2 shows an arrangement according to the invention of two abluminal layers 3, 3a and three anchoring layers 5, 5a and 5b on the surface of the strut 1. Each abluminal layer 3, 3a is disposed so that it is fastened in the transition region 7 between two anchoring layers 5 and 5a, or 5a and 5b, respectively. In this way, particularly good protection of the abluminal layers 3, 3*a* against delamination and shearing is achieved, in particular during the dilation of the stent 10 in the treated hollow organ.

Figure 5:
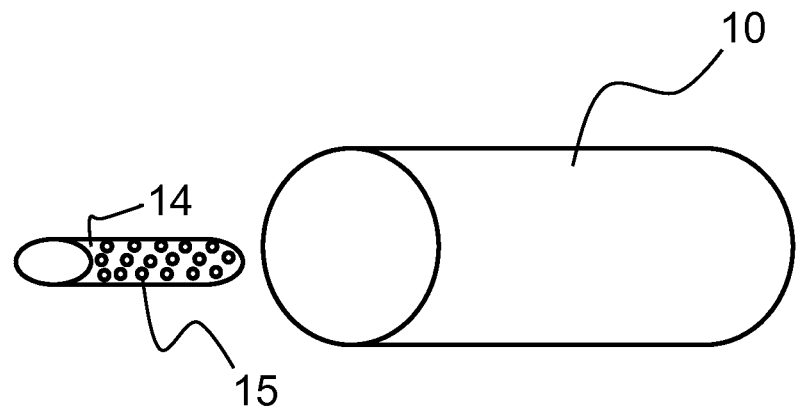

FIG. 5 shows a further possibility of applying the luminally disposed anchoring layer 5. A tubular spray nozzle 14 is introduced in the stent 10, the nozzle comprising a plurality of openings 15 on the entire circumference over a predetermined part of the length thereof, with the dissolved polymer being sprayed through these openings substantially in a radial direction onto the luminal side of the stent 10.

Figure 6:
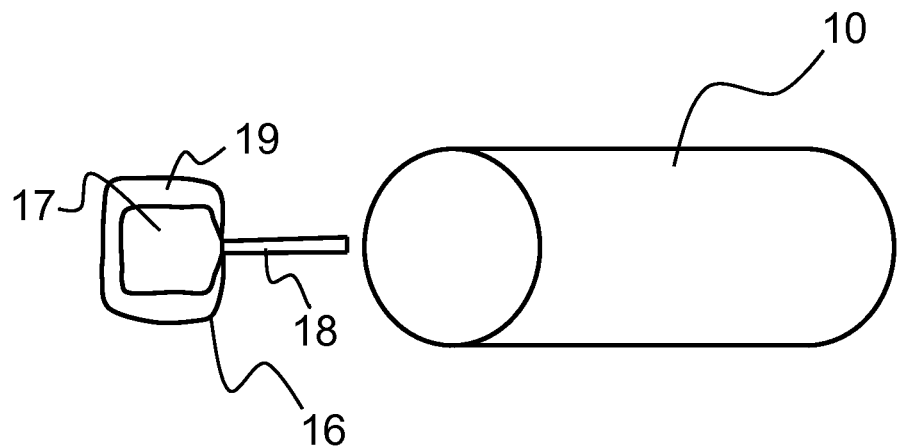

A further possibility for applying the anchoring layer 5 is shown in FIG. 6. An applicator wand 16 comprising a head 17, which is fastened to a thin wire or shaft 18, is used as the means for applying the anchoring layer 5. An absorbent material 19 is disposed on the outer surface of the head 17. This absorbent material 19 is saturated with the polymer solution, for example PLLA (L210; Boehringer Ingelheim) in chloroform, and pulled through the stent 10 by the shaft 18. The diameter of the head 17 comprising the absorbent material 19 of the applicator wand 16 is selected so that the lateral surface of the absorbent material 19 comes in contact with the luminal surface of the stent 10 when the application rod 16 is pulled through, thereby wiping off the polymer solution on the luminal surface of the stent 10. After the solvent has been evaporated, the unloaded polymer remains on the luminal side of the stent 10. However, the solvent, chloroform, has partially dissolved the abluminal layer 3 in the transition region 7, for example in the embodiment shown in FIG. 1, and created a stable connection between the abluminal layer 3 and luminal anchoring layer 5. The positive engagement obtained in this way results in improved mechanical properties. In particular, delamination of the abluminal layer 3 was no longer observed.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMERALS

1 Strut of a stent
3, 3*a* Abluminal layer
5, 5*a*, 5*b* Anchoring layer
7 Transition region
9 Further layer
10 Stent
11 Pipetting nozzle for applying the abluminal layer 3
13 Pipetting nozzle for applying the anchoring layer 5
14 Tubular spray nozzle
15 Opening
16 Applicator wand
17 Head
18 Shaft
19 Absorbent layer

What is claimed is:

1. An implant in the form of an intraluminal endoprosthesis, comprising:
   a body;
   an abluminal layer disposed on the abluminal surface of the body and formed from a polymer formulation, wherein the abluminal layer optionally contains at least one pharmaceutically active substance; and
   an anchoring layer disposed on the luminal surface of the body and formed from a different polymer formulation that degrades more quickly in vivo than the polymer formulation forming the abluminal layer, wherein opposing ends of the anchoring layer are coupled to opposing ends of the abluminal layer at opposing transition regions, further wherein the abluminal layer is absent from the luminal surface between the opposing transition regions and the anchoring layer is absent from the abluminal surface between the opposing transition regions.

2. The implant according to claim 1, characterized in that the transition regions are less than 30% of the total surface of the abluminal layer.

3. The implant according to claim 1, characterized in that the anchoring layer extends in the luminal region of the implant.

4. The implant according to claim 1, characterized in that the abluminal layer is degradable.

5. The implant according to claim 1, characterized in that the abluminal layer is joined to the anchoring layer in the transition region by a bond, a positive engagement or both.

6. The implant according to claim 1, characterized in that n abluminal layers are disposed in the transition region between two of the n+1 anchoring layers, with n>=1 and n being an integer.

7. The implant according to claim 1, characterized in that a further coating is disposed on at least part of the surface of the anchoring layer, the further coating optionally comprising one or more selected from of the group consisting of an endothelial cell capturing technology, an endothelialization promoter and an endothelialization-promoting surface.

8. The implant according to claim 1, further comprising a second anchoring layer, wherein the abluminal layer is embedded within both anchoring layers at the transition regions.

9. An implant according to claim 1, wherein the abluminal layer is fastened at the opposing transition regions.

10. An implant in the form of an intraluminal endoprosthesis, comprising:
    a body;
    an abluminal layer disposed on the abluminal surface of the body and formed from a polymer formulation, wherein the abluminal layer optionally contains at least one pharmaceutically active substance; and
    an anchoring layer disposed on the luminal surface of the body and formed from a different polymer formulation than the polymer formulation of the abluminal layer, wherein opposing ends of the abluminal layer and anchoring layer are partially dissolved into one another at opposing transition regions, further wherein the abluminal layer is absent from the luminal surface between the opposing transition regions and the anchoring layer is absent from the abluminal surface between the opposing transition regions.

11. The implant according to claim 10, characterized in that the transition regions are less than 30% of the total surface of the abluminal layer.

12. The implant according to claim 10, characterized in that n abluminal layers are disposed in the opposing transition regions between two of n+1 anchoring layers, with n>=1 and n being an integer.

13. The implant according to claim 10, characterized in that a further coating is disposed on at least part of the surface of the anchoring layer, the further coating comprising one or more selected from of the group consisting of an endothelial cell capturing technology, an endothelialization promoter and an endothelialization-promoting surface.

\* \* \* \* \*